(12) United States Patent
Roggan et al.

(10) Patent No.: US 10,118,145 B2
(45) Date of Patent: Nov. 6, 2018

(54) METHOD FOR THE PHOSGENATION OF COMPOUNDS COMPRISING HYDROXYL, THIOL, AMINO AND/OR FORMAMIDE GROUPS

(71) Applicant: BAYER AKTIENGESELLSCHAFT, Leverkusen (DE)

(72) Inventors: Jens Stefan Roggan, Cologne (DE); Leslaw Mleczko, Dormagen (DE); Konstantinos Metaxas, Cologne (DE); Michael Gottfried, Wuppertal (DE); Ilja Peckermann, Cologne (DE); Stephan Schubert, Leverkusen (DE); Ekkehard Barth, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 15/503,944

(22) PCT Filed: Aug. 18, 2015

(86) PCT No.: PCT/EP2015/068883
§ 371 (c)(1),
(2) Date: Feb. 14, 2017

(87) PCT Pub. No.: WO2016/026826
PCT Pub. Date: Feb. 25, 2016

(65) Prior Publication Data
US 2017/0274341 A1 Sep. 28, 2017

(30) Foreign Application Priority Data

Aug. 20, 2014 (DE) .................. 10 2014 111 903

(51) Int. Cl.
*B01J 8/06* (2006.01)
*C07C 68/02* (2006.01)
(Continued)

(52) U.S. Cl.
CPC .............. *B01J 8/067* (2013.01); *B01J 8/06* (2013.01); *C01B 31/28* (2013.01); *C01B 32/80* (2017.08);
(Continued)

(58) Field of Classification Search
CPC . B01J 2219/00085; B01J 8/067; C01B 31/28; C07C 68/02
See application file for complete search history.

(56) References Cited

U.S. PATENT DOCUMENTS 5,380,909 A 1/1995 Harley et al.
6,348,613 B2 2/2002 Miyamoto et al.
(Continued)

FOREIGN PATENT DOCUMENTS

EP 0 520 238 A1 12/1992
EP 1 112 997 A2 7/2001
(Continued)

OTHER PUBLICATIONS

Mitchell et al. "Selection of Carbon Catalysts for the Industrial Manufacture of Phosgene", Catalysis Science & Technology (2012) vol. 2 pp. 2109-2115.
(Continued)

*Primary Examiner* — Valerie Rodriguez-Garcia
(74) *Attorney, Agent, or Firm* — McBee Moore Woodward & Vanik IP, LLC

(57) ABSTRACT

A method of reacting phosgene with a second compound containing one or more of hydroxyl, thil, amino and/or formamide groups, wherein phosgene has a GHS hazard identification of GHS06 and is obtainable from the reaction of carbon monoxide and chlorine and wherein the second compound is capable of a chemical reaction with phosgene is provided.

11 Claims, 1 Drawing Sheet

(51) Int. Cl.
*C01B 32/80* (2017.01)
*C01B 31/28* (2006.01)

(52) U.S. Cl.
CPC ..... *C07C 68/02* (2013.01); *B01J 2208/00212* (2013.01); *B01J 2208/00309* (2013.01); *B01J 2219/0004* (2013.01); *B01J 2219/00085* (2013.01)

(56) References Cited

U.S. PATENT DOCUMENTS

| | | |
|---|---|---|
| 8,409,539 B2 | 4/2013 | Olbert et al. |
| 8,821,829 B2 | 9/2014 | Olbert et al. |
| 9,023,300 B2 | 5/2015 | Olbert et al. |
| 2001/0041806 A1 | 11/2001 | Miyamoto et al. |
| 2005/0118088 A1 | 6/2005 | Olbert et al. |
| 2011/0288334 A1 | 11/2011 | Olbert et al. |
| 2013/0072717 A1 | 3/2013 | Olbert et al. |
| 2013/0099166 A1 | 4/2013 | Shashi et al. |
| 2013/0303783 A1 | 11/2013 | Pilia et al. |

FOREIGN PATENT DOCUMENTS

| | | |
|---|---|---|
| WO | 2003/072237 A1 | 9/2003 |
| WO | 2010/076208 A1 | 7/2010 |

OTHER PUBLICATIONS

International Search Report of PCT/EP2015/068883 dated Nov. 19, 2015.

METHOD FOR THE PHOSGENATION OF COMPOUNDS COMPRISING HYDROXYL, THIOL, AMINO AND/OR FORMAMIDE GROUPS

CROSS REFERENCE TO RELATED APPLICATIONS

This application is a § 371 National Stage Application of PCT/EP2015/068883, filed Aug. 18, 2015, which claims priority to German Application No. 10 2014 111 903.7, filed Aug. 20, 2014.

BACKGROUND OF THE INVENTION

Field of the Invention

The studies that led to this invention were supported under Grant Agreement No. 245988 as part of the Seventh Framework Programme of the European Union (FP7/2007-2013).

The present invention relates to a method of reacting a first compound with a second compound, wherein the first compound has a GHS hazard identification of GHS06 and is obtainable from the reaction of at least one first fluid precursor compound and one second fluid precursor compound and wherein the second compound is capable of a chemical reaction with the first compound. More particularly, the method is a phosgenation method for aromatic alcohols. It further relates to a reactor suitable for performing the method of the invention.

Phosgene ($COCl_2$) is a key reagent in the production of pharmaceuticals, polyurethanes and polycarbonates. It is a very reactive but also very toxic chemical, and the industrial scale production process, because of the amounts of phosgene (hold-up) present in a plant, always harbors risks to the environment in the event of an unintended release resulting from leaks in pipelines or other damage to plant components.

Description of Related Art

One example of the industrial scale use of phosgene as key reagent is the preparation of diphenyl carbonate (DPC). DPC is an important intermediate for the synthesis of high-quality polycarbonates, for example through transesterification with bisphenol A. The synthesis of DPC proceeding from phenol and phosgene (direct phosgenation) proceeds in two steps: the first step comprises the preparation of phosgene in a gas phase reaction of carbon monoxide and chlorine, which typically proceeds or is conducted over activated carbon catalysts in a multitube fixed bed reactor. According to the boiling temperature of the cooling medium in the reactors, a distinction is made between phosgene preparation in cold combiners or hot combiners. By reaction of phenol with phosgene in the presence of a suitable catalyst, DPC is ultimately obtained. DPC preparation via direct phenol phosgenation, in comparison with the conventional interfacial method (reaction of sodium phenoxide with phosgene), offers the advantage that the formation of large amounts of NaCl waste products is avoided.

Both the phosgene synthesis and the DPC synthesis are highly exothermic reactions with enthalpies of reaction of −107 and −54 kJ/mol. Particularly the exothermicity of the phosgene synthesis in the gas phase requires efficient cooling systems, but it is not possible to prevent hotspots in the reactor with local temperatures of more than 500° C. (cf. Mitchell et al., Catal. Sci. Technol., 2012). The occurrence of temperatures of more than 300° C. does not just lead to elevated material stress in the reactor but also adversely affects the equilibrium reaction of phosgene formation (the breakdown of phosgene predominates at more than 300° C.) and additionally increases the rate of deactivation of the catalyst, such that there is an overall drop in space-time yield and process efficient.

WO 2003/072237 A1 discloses a reactor for preparation of phosgene by gas phase reaction of carbon monoxide and chlorine in the presence of a fixed bed catalyst, having a bundle of contact tubes arranged in parallel in the longitudinal direction of the reactor that are secured in tube plates at their ends, having a hood at either end of the reactor, and having deflecting plates which are arranged at right angles to the longitudinal direction of the reactor in the interspace between the contact tubes and which leave alternating opposite passage orifices clear at the inner wall of the reactor, wherein the contact tubes are filled with the fixed bed catalyst, the gaseous reaction mixture is guided from one end of the reactor via a hood through the contact tubes and is drawn off from the opposite end of the reactor via the second hood, and a liquid heat exchange medium is guided through the interspace around the contact tubes, wherein the reactor is free of tubes in the region of the passage orifices.

The process described with this reactor also produces large amounts of phosgene, but these are converted further at a different place and time.

US 2013/303783 A1 relates to a continuous process for preparing CO and $Cl_2$ and the consumption of the phosgene thus generated in a liquid phase reaction in order to obtain organic products P. The process is implemented in two successive reactors R1 and R2, wherein the first reactor R1 is a reactor for the catalytic synthesis of phosgene from CO and $Cl_2$ gas and the second reactor is a piston reactor having a mechanical stirrer unit.

Considering the present state of development, a need for a method with reduced phosgene hold-up is apparent. In the context of the present invention, such a method is provided. More particularly, it was an object of the present invention to provide a phosgenation method in which minimum amounts of free phosgene are present in the reaction system.

SUMMARY

This object is achieved in accordance with the invention by a method of reacting a first compound with a second compound,
wherein the first compound has a GHS hazard identification of GHS06 and is obtainable from the reaction of at least one first fluid precursor compound and one second fluid precursor compound
and wherein the second compound is capable of a chemical reaction with the first compound,
comprising the steps of:
(I) providing a liquid phase containing the second compound in a reactor having an upper end and a lower end viewed in the direction of gravity;
(II) providing a contact tube having an upper end and a lower end in the reactor, wherein
the lower end of the contact tube is immersed into the liquid phase containing the second compound and
a catalyst bed present in the contact tube is set up to catalyze the reaction between the first and second precursor compounds to give the first compound;
(III) introducing the first and second precursor compounds through the contact tube, with the first compound formed in the contact tube exiting from the lower end of the contact tube and coming into contact with liquid phase containing the second compound.

DETAILED DESCRIPTION OF A PREFERRED EMBODIMENT

Figure 1:
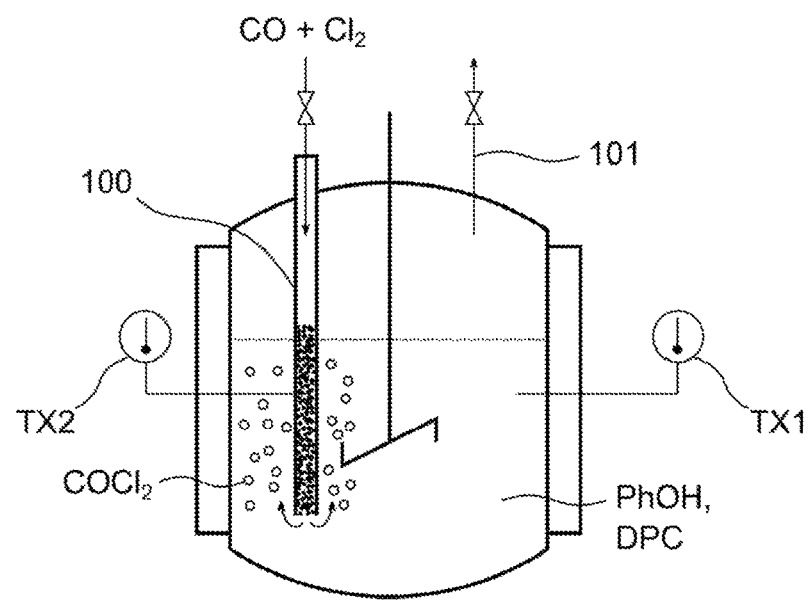
FIGS. 1-2 depict embodiments as described herein

It is envisaged in accordance with the invention that the first compound has a hazard identification according to GHS (Globally Harmonized System of Classification, Labelling and Packaging of Chemicals of the United Nations) of GHS06. In the European Union, this is legislated for by Directive (EC) No. 1272/2008, also called CLP Regulation. The classification GHS06 refers to toxic or very toxic substances.

With regard to the first fluid precursor compound and the second fluid precursor compound, gases and liquids are envisaged in accordance with the invention, including solutions of solids in a solvent.

More particularly, the first compound may be phosgene, the first fluid precursor compound may be carbon monoxide, the second fluid precursor compound may be chlorine, the catalyst present in the catalyst bed may be an activated carbon catalyst and the second compound may be a compound containing hydroxyl, thiol, amino and/or formamide groups.

It is further preferable that the activated carbon catalyst has a BET surface area of ≥300 to ≤2000 $m^2$/g and a $d_{90}$ of the particle size distribution of 25 μm to 4 mm. The BET surface area is more preferably within a range from ≥800 to ≤1200 $m^2$/g; the $d_{90}$ of the particle size distribution is within a range of ≥25 μm to ≤4 mm. On a smaller reaction scale, more particularly, a $d_{90}$ of the particle size distribution of ≥40 μm to ≤120 μm is favorable; on the industrial scale, favorable activated carbon extrudates are those having a $d_{90}$ of the particle size distribution of ≥1 mm to ≤4 mm.

Because of the major importance of the reaction of phosgene with a compound containing hydroxyl, thiol, amino and/or formamide groups, the present invention is elucidated in connection with this first and second compound, but without being restricted thereto.

In the method of the invention, phosgene occurs only as a comparatively short-lived intermediate. The gas mixture of carbon monoxide and chlorine reacts on passage through a contact tube to give phosgene. The phosgene formed in situ exits at the lower end of the contact tube, rises upward and reacts with the compound containing hydroxyl, thiol, amino and/or formamide groups.

The method of the invention can avoid the presence of any great amounts of phosgene in the reaction system. The compound containing hydroxyl, thiol, amino and/or formamide groups also serves to remove the heat of reaction. In addition, the formation of NaCl as by-product is avoided with respect to the conventional phase transfer method. Chlorine can be recovered from the HCl formed via known recycling methods. Overall, the integration of two reactions in one method results in an increase in the space-time yield of the method over a longer period and the thermal stress on the plant is reduced.

In step (I) of the method of the invention, a liquid phase is provided. This may especially comprise molten reactant or reactant dissolved in a solvent. The design of the reactor is not stipulated further at first and may, for example, be a tubular reactor for continuous operation or a tank reactor for a batchwise mode of operation. The reactor has an upper end and a lower end, referenced to the direction of gravity.

Step (II) of the method of the invention comprises the provision of (at least) one contact tube in the reactor, the contact tube likewise having an upper end and a lower end in relation to the direction of gravity. The lower end of the contact tube is immersed here into the liquid phase. For optimization of the process efficiency, the contact tube can be immersed as far as possible into the liquid phase.

In step (III) of the method of the invention, carbon monoxide and chlorine are introduced into the contact tube and react therein to give phosgene. As a result of the gas pressure of the reactant gases, the gaseous phosgene exits at the lower end of the contact tube, comes into contact with the liquid phase and rises upward. The reaction takes place here with the compound containing hydroxyl, thiol, amino and/or formamide groups.

Through the choice of suitable liquid and gas pressures in the two reaction spaces, the passage of liquid reactants into the interior of the contact tube can be prevented.

The base of the contact tube may be formed, for example, by a membrane or a frit.

Examples of suitable compounds containing hydroxyl, thiol, amino and/or formamide groups are aromatic alcohols such as phenol, aliphatic alcohols, primary aromatic amines, secondary aromatic amines, primary aliphatic amines, secondary aliphatic amines, N,N-dimethylformamide and N-methylformanilide. Especially aromatic and aliphatic alcohols and formamides are preferred; the former because of the use of the reaction products in polycarbonate production and the latter because of their use in Vilsmeier-Haack formylations. Preference is further given to primary amines, since they can be converted by phosgenation to the corresponding isocyanates which are used in polyurethane production.

Overall, the contact tube may also be regarded as a fixed bed reactor for a gas reaction.

Corrosion-sensitive surfaces in the reactor can be protected, for example, by means of a stainless steel or $SiO_2$ coating.

With regard to the reaction conditions in the method of the invention, the reaction temperature for the phosgene synthesis may advantageously be between 80 and 300° C. and for the phosgenation (especially of phenol) between 80 and 300° C. Particular preference is given to a reaction temperature in the liquid phase in the reactor of 190 to 210° C.

In order that the liquid phase can serve particularly effectively as heat removal medium, it is favorable when the temperature for the phosgene synthesis and the temperature in the liquid phase differ from one another by not more than 20° C., 10° C. or 5° C. It is particularly favorable when the temperature of the phosgene synthesis (within the typical process-related fluctuations) is equal to the temperature in the liquid phase.

Preference is given to a molar excess of phenol of ≥4 to ≤6.

Further embodiments and aspects of the present invention are elucidated hereinafter. They can be combined with one another as desired unless the opposite is apparent from the context.

In one embodiment of the method of the invention, the method is conducted in a reactor comprising:
a hood at the upper end of the reactor, bounded by a tube plate within the reactor;

a multitude of contact tubes arranged in longitudinal direction of the reactor, the contact tubes being secured on the tube plate by their upper ends, and wherein the liquid phase containing the second compound is provided in the interspace around the contact tubes.

In a further embodiment of the method of the invention, a catalyst is additionally present in the liquid phase containing the second compound. The catalyst, especially for the reaction of phosgene with the compound containing hydroxyl, thiol, amino and/or formamide groups, is preferably dissolved in the reaction medium present in the second reaction space. In the case of the phosgenation of aromatic alcohols such as phenol, it is possible to use $TiCl_4$ or pyridine, for example.

In a further embodiment of the method of the invention, the compound containing hydroxyl, thiol, amino and/or formamide groups is phenol, dimethylformamide or N-methylformanilide.

In a further embodiment of the method of the invention, the contact tube(s) has/have a ratio of length to diameter of $\geq 15:1$ to $\leq 1600:1$. Preferably, the ratio is within a range from $\geq 50:1$ to $\leq 350:1$.

In a further embodiment of the method of the invention, the sum total of the partial pressures of the first precursor compound and the second precursor compound is $\geq 1$ bar to $\leq 26$ bar. Preference is given to a sum total of these partial pressures of $\geq 11$ to $\leq 15$ bar. Irrespective of this, it is preferable that the pressure in the part of the reactor containing the liquid phase containing the second compound is $\geq 3$ to $\leq 6$ bar, especially $\geq 4$ to $\leq 5$ bar, lower than the sum total of the partial pressures of the first precursor compound and the second precursor compound.

The invention further relates to a reactor for reaction of phosgene with compounds containing hydroxyl, thiol, amino and/or formamide groups, comprising:

a hood at the upper end of the reactor, bounded by a tube plate within the reactor;

a multitude of contact tubes arranged in longitudinal direction of the reactor, the contact tubes being secured on the tube plate by their upper ends, wherein a catalyst bed present in the contact tubes is set up to catalyze the reaction of carbon monoxide and chlorine;

the reactor is set up to introduce carbon monoxide and chlorine gas into the space formed between the hood and tube plate, such that these gases flow through the contact tubes;

the reactor is set up to introduce a compound containing hydroxyl, thiol, amino and/or formamide groups into the interspace around the contact tubes and to withdraw liquid reaction products of this compound with phosgene from this interspace and the reactor is additionally set up to withdraw gaseous reaction products on the side of the tube plate facing away from the hood.

In one embodiment of the reactor of the invention, the activated carbon catalyst has a BET surface area of $\geq 300$ to $\leq 2000$ m$^2$/g and a $d_{90}$ of the particle size distribution of 25 μm to 4 mm. The BET surface area is more preferably within a range from $\geq 800$ to $\leq 1200$ m$^2$/g; the $d_{90}$ of the particle size distribution is within a range of $\geq 25$ μm to $\leq 4$ mm. On a smaller reaction scale, more particularly, a $d_{90}$ of the particle size distribution of $\geq 40$ μm to $\leq 120$ μm is favorable; on the industrial scale, favorable activated carbon extrudates are those having a $d_{90}$ of the particle size distribution of $\geq 3$ mm to $\leq 4$ mm.

In a further embodiment of the reactor of the invention, the contact tubes have a ratio of length to diameter of $\geq 15:1$ to $\leq 1600:1$. Preferably, the ratio is within a range from $\geq 50:1$ to $\leq 350:1$.

The present invention is elucidated in detail by the figures and examples which follow, but without being limited thereto. The figures show:

FIG. 1 a cross section through a reactor for the method of the invention

Figure 2:
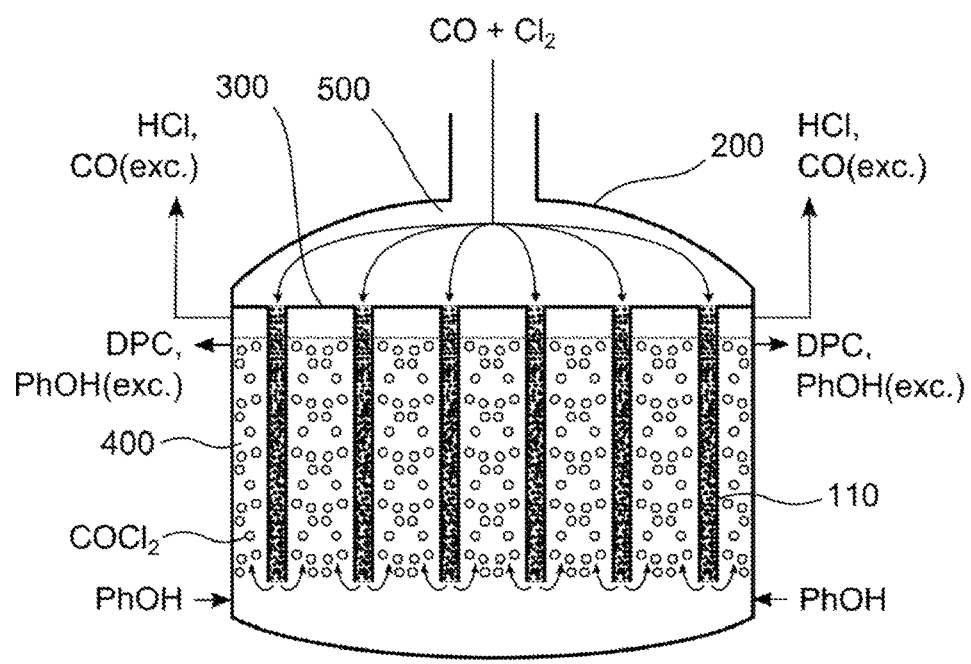

FIG. 2 a cross section through a reactor of the invention

FIG. 1 shows a schematic cross section through a reactor in which the method of the invention is conducted. A stirred tank reactor with a lateral heating/cooling jacket was charged with molten phenol. The height of the liquid level is illustrated by the dotted line in the reactor. A contact tube 100 with an activated carbon fixed catalyst bed is arranged within the reactor, with the lower end of the contact tube 100 immersed into the molten phenol.

Via the conduit 101, gas introduced into the reactor can be removed again. The gas may, for example, be nitrogen when the reactor is inertized prior to commencement of the reaction. In addition, substances can be introduced into the reactor via the conduit 101. These may especially be catalysts for the preparation of DPC, for example $TiCl_4$.

The temperature sensor TX1 measures the temperature in the liquid phase within the reactor. The temperature within the contact tube is measured by the temperature sensor TX2.

As carbon monoxide and chlorine pass through the contact tube 100, phosgene is formed, which exits from the lower end of the contact tube 100 in the form of gas bubbles and rises upward through the phenol. In the course of this, DPC is formed.

FIG. 2 shows a schematic cross section through a reactor of the invention in which the method of the invention is conducted. At its upper end, viewed in relation to the direction of gravity, is a hood 200. Also present within the reactor is a tube plate 300 which bounds the hood 200 in the interior. This forms a gas space 500.

The tube plate 300 bears a plurality of contact tubes 110 secured by their upper ends in the tube plate 300. The contact tubes 110 are arranged in longitudinal direction of the reactor. On the side remote from the tube plate 300, the contact tubes 110 form an interspace 400.

The interspace 400 is charged with liquid phenol. The height of the liquid level is illustrated by the dotted line in the reactor. Carbon monoxide and chlorine gas are introduced simultaneously into the hood 200, mix in the space 500 pass through the orifices into the contact tubes 110 at the upper end thereof. As already outlined above, phosgene is formed in the contact tubes 110, exits from the lower ends of the contact tubes 110 at the orifices, rises upward through the phenol and reacts with the phenol as it does so to form DPC.

At the upper end of the liquid level, DPC and excess phenol ("PhOH(exc.)") are withdrawn. Above the liquid level, on the side of the tube plate 300 facing away from the hood 200, the gaseous HCl and excess carbon monoxide ("CO(exc.)") components are withdrawn.

The tube plate 300 has no further orifices aside from the orifices which are formed by the upper ends of the contact tubes 110. In this way, the gas space 500 can be separated from the interspace 400. This has the advantage that contact of chlorine gas with phenol and the formation of chloroaromatics as by-products can be avoided.

EXAMPLES

Performance of the method of the invention on the laboratory scale

The experimental setup was analogous to the schematic arrangement shown in FIG. 1. A 600 mL pressure reactor equipped with a sparging stirrer and internal thermometer (cf. TX1 in FIG. 1) was charged with 280.4 g (2.98 mol) of phenol and the latter was melted by heating to about 45-50° C. The catalyst cartridge (cf. 100 in FIG. 1; length: 118 mm, diameter: 12 mm) was charged with 2.59 g of activated carbon powder (particle size 45-125 μm) and screwed to the lid of the pressure vessel in a gas-tight manner. The base of the cartridge was provided with a hole (diameter 0.5 mm). In a stream of nitrogen, the reactor lid provided with the integrated catalyst cartridge (cf. 100 in FIG. 1) was screwed on and hence the catalyst cartridge was immersed into the phenol melt. The internal cartridge temperature was measured by means of a further thermocouple (cf. TX2 in FIG. 2) in a central cartridge position. The reactor outlet (cf. conduit 101 in FIG. 1) was still open at this time and the reactor was inertized by the constant $N_2$ stream (6.0 mL/min) while stirring for 30 min. Subsequently, through the valve present in this conduit (cf. conduit 101 in FIG. 1), 0.1 mL of $TiCl_4$ was added to the liquid PhOH. The mixture was heated to 200° C. under a constant $N_2$ flow (6.0 mL/min). The reactor outlet valve (cf. conduit 101 in FIG. 1) was closed here at an internal temperature of TX1=130° C. On attainment of internal reactor temperature 200° C., 4.5 mL/min of CO and 4.3 mL/min of $Cl_2$ were metered in with simultaneous stoppage of the addition of $N_2$ (catalyst cartridge; cf. 100 in FIG. 1). After introduction of a total of 1.12 L of CO (0.050 mol) and 1.06 L of $Cl_2$ (0.047 mol), the addition of $Cl_2$ and CO was ended and switched to 3.0 mL/min of $N_2$. The pressure in the reactor at this time was 12 bar. The reaction mixture was stirred at 200° C. for 60 minutes and then cooled down to 50° C. over several hours. On attainment of 120° C., the reactor was decompressed. Under a still constant stream of $N_2$ (3.0 mL/minute) and while stirring (2000 rpm), the reactor was inertized overnight and freed of possible residues of HCl, $COCl_2$, CO or $Cl_2$. The formation of DPC was detected by analysis of the product mixture obtained by means of gas chromatography.

The invention claimed is:

1. A method of reacting a first compound with a second compound,
    wherein the first compound has a GHS hazard identification of GHS06 and is obtainable from the reaction of at least one first fluid precursor compound and one second fluid precursor compound and
    wherein the second compound is capable of a chemical reaction with the first compound, comprising:
    (I) providing a liquid phase containing the second compound in a reactor having an upper end and a lower end viewed in the direction of gravity;
    (II) providing a contact tube having an upper end and a lower end in the reactor,
        wherein the lower end of the contact tube is immersed into the liquid phase containing the second compound and a catalyst bed present in the contact tube is set up to catalyze the reaction between the first and second precursor compounds to give the first compound;
    (III) introducing the first and second precursor compounds through the contact tube, with the first compound formed in the contact tube exiting from the lower end of the contact tube and coming into contact with liquid phase containing the second compound,
        wherein the first compound is phosgene, the first precursor compound is carbon monoxide, the second precursor compound is chlorine, the catalyst present in the catalyst bed is an activated carbon catalyst and the second compound is a compound containing one or more of hydroxyl, thiol, amino and/or formamide groups.

2. The method as claimed in claim 1, wherein the activated carbon catalyst has a BET surface area of ≥300 to ≤2000 $m^2/g$ and a $d_{90}$ of the particle size distribution of 25 μm to 4 mm.

3. The method according to claim 1, wherein the method is conducted in a reactor comprising:
    a hood at the upper end of the reactor, bounded by a tube plate within the reactor;
    a multitude of contact tubes arranged in longitudinal direction of the reactor, the contact tubes being secured on the tube plate by upper ends thereof;
        and wherein the liquid phase containing the second compound is provided in an interspace around the contact tubes.

4. The method as claimed in claim 1, wherein a catalyst is additionally present in the liquid phase containing the second compound.

5. The method as claimed in claim 1, wherein the contact tube has/have a ratio of length to diameter of ≥15:1 to ≤1600:1.

6. The method as claimed in claim 1, wherein the sum total of the partial pressures of the first precursor compound and the second precursor compound is ≥1 bar to ≤26 bar.

7. The of claim 1, wherein the second compound is phenol.

8. The method as claimed in claim 1, wherein the second compound is a compound containing one or more hydroxyl groups.

9. The method as claimed in claim 1, wherein the second compound is a compound containing one or more thiol groups.

10. The method as claimed in claim 1, wherein the second compound is a compound containing one or more amino groups.

11. The method as claimed in claim 1, wherein the second compound is a compound containing one or more formamide groups.

* * * * *